United States Patent [19]

Mich et al.

[11] Patent Number: 4,663,457

[45] Date of Patent: May 5, 1987

[54] 1-CYCLOPROPYL-6,7-DIHALO-1,4-DIHYDRO-4-OXO-1,8-NAPHTHYRIDINE-3-CARBOXYLIC ACID AND THEIR ESTERS, USEFUL AS INTERMEDIATES FOR PREPARING THE 7-AMINE SUBSTITUTED NAPHTHYRIDINES

[75] Inventors: Thomas F. Mich, Ann Arbor; Joseph P. Sanchez; John M. Domagala, both of Canton; Ashok K. Trehan, Ann Arbor, all of Mich.

[73] Assignee: Warner-Lambert Company, Morris Plains, N.J.

[21] Appl. No.: 765,099

[22] Filed: Aug. 13, 1985

Related U.S. Application Data

[60] Division of Ser. No. 692,819, Jan. 23, 1985, abandoned, which is a continuation-in-part of Ser. No. 581,410, Feb. 17, 1984, abandoned.

[51] Int. Cl.$^4$ ............................................. C07D 471/04
[52] U.S. Cl. .................................................... 546/123
[58] Field of Search ................................ 546/123, 156

[56] References Cited

U.S. PATENT DOCUMENTS 3,849,421  11/1974  Nakagome et al. ................. 546/123

FOREIGN PATENT DOCUMENTS 0004279  10/1979  European Pat. Off. ............ 546/123
132845  2/1985  European Pat. Off. ............ 546/123

OTHER PUBLICATIONS

Matsumoto et al., J. Med. Chem. vol. 27, No. 3, 292–301 1984.
Matsumoto et al., Current Chemotherapy and Infectious Disease, vol. 1. pp. 455–456, 19th ICAAC Mar., J. Adv. Org. Chem. p. 208.

*Primary Examiner*—John M. Ford
*Assistant Examiner*—J. Richter
*Attorney, Agent, or Firm*—Ronald A. Daignault

[57] ABSTRACT

1-cyclopropyl-6,7-dihalo-1,4-dihydro-4-oxo-1,8-naphthyridine-3-carboxylic acids and their esters, which are useful as intermediates for the preparation of compounds which are useful as anti-bacterial agents.

3 Claims, No Drawings

1-CYCLOPROPYL-6,7-DIHALO-1,4-DIHYDRO-4-OXO-1,8-NAPHTHYRIDINE-3-CARBOXYLIC ACID AND THEIR ESTERS, USEFUL AS INTERMEDIATES FOR PREPARING THE 7-AMINE SUBSTITUTED NAPHTHYRIDINES

CROSS-REFERENCE TO RELATED APPLICATION

This application is a division of U.S. Ser. No. 692,819, filed Jan. 23, 1985, now abandoned, which application is a continuation-in-part of U.S. Ser. No. 581,410 of Feb. 17, 1984, now abandoned.

BACKGROUND OF THE INVENTION

The Journal of Medicinal Chemistry, 23, 1358 (1980) discloses certain substituted quinoline-3-carboxylic acids having the structural formula.

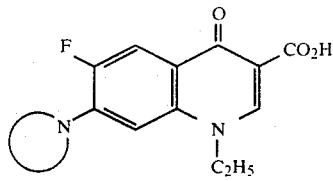

See also U.S. Pat. No. 4,146,719.

European Patent Publication No. 78362 describes 1-cyclopropyl-6-fluoro-1,4-dihydro-4-oxo-7-piperazinoquinoline-3-carboxylic acids.

Certain 7-heterocyclic substituted 1,8-naphthyridines are disclosed in Eur. J. Med. Chem.-Chimica Therapeutica, 29, 27 (1977).

The above references teach that these compounds possess antibacterial activity.

SUMMARY OF THE INVENTION

The present invention relates to a compound of the formula

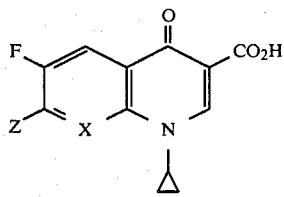

wherein Z is a group of the formula

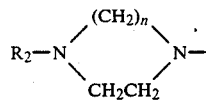

where n is 2–3 and $R^2$ is hydrogen, lower alkyl or acetyl,

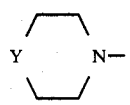

where Y is O or S, or

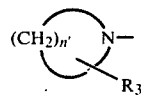

where $n'$ is 4–6 and $R^3$ is hydrogen or hydroxyl; X is CF, or N; $R^1$ is hydrogen or lower alkyl, or a pharmaceutically acceptable acid-addition or base salt thereof.

The present invention includes, as novel intermediates, 1-cyclopropyl-6,7,8-trifluoro-1,4-dihydro-4-oxo-3-quinolinecarboxylic acid, 1-cyclopropyl-6,7-difluoro-1,4-dihydro-4-oxo-1,8-naphthyridine-3-carboxylic acid, and 1-cyclopropyl-6-fluoro-7-chloro-1,4-dihydro-4-oxo-1,8-naphthyridine-3-carboxylic acid as well as lower alkyl esters or salts thereof.

The invention also includes a pharmaceutical composition which comprises an antibacterially effective amount of a compound having structural formula I and the pharmaceutically acceptable acid-addition or base salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the invention having the structural formula I may be readily prepared by treating a corresponding compound having the structural formula II

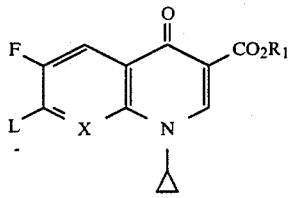

wherein $R_1$ and X are as defined above and L is a leaving group, preferably fluorine or chlorine with an amine corresponding to the group Z.

If the group Z contains an alkylamine substituent, said substituent may, if desired, be protected by a group which renders it substantially inert to the reaction conditions. Thus, for example, protecting groups such as the following may be utilized:

carboxylic acyl groups such as formyl, acetyl, trifluoroacetyl;

alkoxycarbonyl groups such as ethoxycarbonyl, t-butoxycarbonyl, β,β,β-trichloroethoxycarbonyl, β-iodoethoxycarbonyl;

aryloxycarbonyl groups such as benzyloxycarbonyl, p-methoxybenzyloxycarbonyl, phenoxycarbonyl;

silyl groups such trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized.

The protecting group may be removed, after the reaction if desired, by procedures known to those skilled in the art. For example, the ethoxycarbonyl group may be removed by acid or base hydrolysis and the trityl group may be removed by hydrogenolysis.

The reaction between the compound of structural formula II and a suitably protected amine, if necessary, of group Z may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the amine of the group Z may be utilized as the acid acceptor.

Convenient solvents for this reaction are non-reactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group may be accomplished either before or after isolating the product.

Alternatively, the compound of formula I wherein X is N, $R_1$ is hydrogen and Z is piperazine may be prepared by removal of its precursor carboethoxypiperazine derivative and/or ester thereof. The piperazine may then be alkylated by known means to form the lower alkyl piperazine derivatives of formula I.

The above compound, namely 1-cyclopropyl-6-fluoro-1,4-dihydro-4-oxo-7-(1-piperazinyl)-1,8-naphthyridine-3-carboxylic acid, its 4-lower alkylpiperazinyl, or its 4-carboethoxypiperazinyl derivative and/or esters thereof are also useful as intermediates to prepare a compound of formula II wherein X is N and L is fluorine or chlorine. The piperazine groups may be cleaved and displaced by a hydroxyl group by treating with a mixture of nitric and sulfuric acids, which hydroxyl compound is further displaced by group L, fluorine, or chlorine. For example, treatment of the hydroxyl compound with phosphorus-oxychloride under known conditions affords the chloro compound of formula II.

The starting material 1-cyclopropyl-6-fluoro-1,4-dihydro-4-oxo-7-[1-(4-carboethoxy)piperazinyl]1,8-naphthyridine-3-carboxylic acid and its ethyl ester may be prepared as described in the Preparative Examples.

The starting compound of formula II, wherein X is CF and L is F, namely 1-cyclopropyl-6,7,8-trifluoro-1,4-dihydro-4-oxo-3-quinolinecarboxylic acid may be prepared by a series of reactions starting from 2,3,4,5-tetrafluorobenzoic acid and detailed also in the Preparative Examples. The acid chloride of 2,3,4,5-tetrafluorobenzoic acid is reacted with dilithium salt of malonic acid half ethyl ester to afford after hydrolysis 2,3,4,5-tetrafluoro-β-oxobenzenepropanoic acid, ethyl ester. This compound is, in turn, treated with triethylorthoformate and acetic anhydride, cyclopropylamine, potassium t-butoxide, and aqueous hydrochloric acid to give the desired intermediate.

The amines corresponding to group Z are known and either commercially available or capable of being prepared by methods known in the art.

The compounds of the invention display antibacterial activity when tested by the microtitration dilution method as described in Heifetz, et al, Antimicr. Agents & Chemoth., 6, 124 (1974), which is incorporated herein by reference.

By use of the above referenced method, the followed minimum inhibitory concentration values (MICs in μg/ml) were obtained for representative compounds of the invention.

| | IN VITRO ANTIBACTERIAL ACTIVITY Minimal Inhibitory Concentration MIC (μg/ml) | | | |
|---|---|---|---|---|
| Organisms | Compound Ex. 1 | Compound Ex. 2 | Compound Ex. 3 | Compound Ex. 4 |
| *Enterobacter cloacae* MA 2646 | 0.1 | ≦0.1 | ≦0.1 | 0.2 |
| *Escherichia coli* Vogel | ≦0.1 | ≦0.1 | ≦0.1 | 0.1 |
| *Klebsiella pneumoniae* MGH-2 | 0.1 | ≦0.1 | ≦0.1 | 0.05 |
| *Proteus rettgeri* M 1771 | 0.2 | 0.4 | ≦0.1 | 0.2 |
| *Pseudomonas aeruginosa* UI-18 | 0.2 | 0.4 | 0.2 | 0.8 |
| *Staphylococcus aureus* H 228 | 1.6 | 0.4 | 0.4 | 0.025 |
| *Staphylococcus aureus* UC-76 | 0.4 | 0.1 | ≦0.1 | 0.013 |
| *Streptococcus faecalis* MGH-2 | 1.6 | 0.8 | 0.4 | 0.1 |
| *Streptococcus pneumoniae* SV-1 | 1.6 | 6.3 | 0.8 | 0.4 |
| *Streptococcus pyogenes* C-203 | 1.6 | 3.1 | 0.4 | 0.4 |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where $R_1$ is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The term "lower alkyl" contemplates an alkyl group of both straight and branched carbon chains of from one to about three carbon atoms except when specifically stated to be greater than three carbon atoms. Representative of such groups are methyl, ethyl, propyl, isopropyl, and the like.

Certain compounds of the invention may exist in optically active forms. The pure D isomer, pure L isomer as well as mixtures thereof; including the racemic mixtures, are contemplated by the invention. Additional assymmetric carbon atoms may be present in a substituent such as an alkyl group. All such isomers as well as mixtures thereof are intended to be included in the invention.

A preferred class of compounds of the present invention are those of formula I where Z is 1-piperazinyl or 4-lower alkyl-1-piperazinyl. Particularly preferred are those compounds of formula I wherein Z is 1-piperazinyl or 4-methyl-1-piperazinyl and their pharmaceutically acceptable salts.

The compounds of the invention can be prepared and administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc.). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantites of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

Route A

1-Cyclopropyl-6-fluoro-1,4-dihydro-4-oxo-7-(1-piperazinyl)-1,8-naphthyridine-3-carboxylic acid A suspension of 0.7 g (1.6 mmole) of ethyl 1-cyclopropyl-6-fluoro-1,4-dihydro-4-oxo-7-[4-(ethoxycarbonyl)-1-piperazinyl]-1,8-naphthyridine-3-carboxylate (see Example H), 6 ml of 10% aqueous sodium hydroxide and 2 ml of ethanol was refluxed for three hours. The reaction was filtered through a fiber glass pad to clarify and acidified to pH 1.5 with 6.0M hydrochloric acid and lyophilized. The residue was dissolved in 10 ml of ammonium hydroxide and the solution concentrated in vacuo. The precipitate which formed was removed by filtration, washed with aqueous ethanol, ether and dried in vacuo to give 0.04 g of the title compound, mp 274°–276° C.

Route B

1-Cyclopropyl-6-fluoro-1,4-dihydro-4-oxo-7-(1-piperazinyl)-1,8-naphthyridine-3-carboxylic acid A solution of 10.2 g (25 mmole) of 1-cyclopropyl-6-fluoro-1,4-dihydro-4-oxo-7-[4-(ethoxycarbonyl)-1-piperazinyl]-1,8-naphthyridine-3-carboxylic acid (see Example J), 100 ml of 10% aqueous sodium hydroxide and 40 ml of ethanol was refluxed for three hours. The solution was concentrated to 125 ml and acidified to pH 7.3 with glacial acetic acid. The resulting precipitate was removed by filtration, washed with 50% aqueous ethanol, ether and dried in vacuo to give 7.2 g of the title compound, mp 274°–276°.

EXAMPLE 2

1-Cyclopropyl-6-fluoro-1,4-dihydro-7-(4-methyl-1-piperazinyl)-4-oxo-1,8-naphthyridine-3-carboxylic acid A suspension of 1.3 g (4.0 mmole) of 1-cyclopropyl-6-fluoro-1,4-dihydro-4-oxo-7-(1-piperazinyl)-1,8-naphthyridine-3-carboxylic acid, 13.3 ml of 37% formalin and 13.3 ml of 88% formic acid was refluxed for four hours. The resulting solution was evaporated in vacuo. The residue was suspended in aqueous ethanol, the resulting precipitate removed by filtration, washed with water and dried in vacuo to give 1.24 g of the title compound, mp 236°–237° C.

EXAMPLE 3

1-Cyclopropyl-6,8-difluoro-1,4-dihydro-4-oxo-7-(1-piperazinyl)-3-quinolinecarboxylic acid To 1.00 g (3.53 mmol) of 1-cyclopropyl-6,7,8-trifluoro-1,4-dihydro-4-oxo-3-quinolinecarboxylic acid in 10.0 ml of acetonitrile and 0.54 g (3.53 mmol) of 1,8-diazobicyclo[5.4.0]undec-7-ene, was added 1.70 g (19.7 mmol) of piperazine. The mixture was refluxed for one hour and then stirred overnight. It was concentrated, dissolved in ammonium hydroxide and filtered. The filtrate was then concentrated to one-half volume and filtered to give 0.67 g of the title compound, mp >270° C.

EXAMPLE 4

1-Cyclopropyl-6,8-difluoro-1,4-dihydro-7-(3-hydroxy-1-pyrrolidinyl)-4-oxo-3-quinolinecarboxylic acid A mixture of 2.1 g (7.8 mmol) of 1-cyclopropyl-6,7,8-trifluoro-1,4-dihydro-4-oxo-3-quinoline carboxylic acid, 20 ml acetonitrile, 1.2 g (7.8 mmole) 1,8-diazobicyclo[5.4.0]undec-7-ene and 0.7 g (7.8 mmole) of 3-hydroxypyrrolidine was refluxed for 2.5 hours. The reaction was allowed to cool and stirred at room temperature for 48 hours. The resulting precipitate was filtered, washed with diethyl ether, then taken up in isopropyl alcohol. The solid was filtered and washed with ether until dry to give 2.0 g of the title compound, mp 276°–278° C.

EXAMPLE 5

The following compounds are prepared by reacting an approximately equimolar amount of 1-cyclopropyl-6,7,8-trifluoro-1,4-dihydro-4-oxo-3-quinolinecarboxylic acid (see Example L) and the desired amine or blocked amine corresponding to group Z in formula I in acetonitrile and an equimolar amount of 1,8-diazobicyclo[5.4.0]undec-7-ene at reflux for one hour, then stirring at room temperature overnight, filtering, washing with diethyl ether and drying:

1-cyclopropyl-6,8-difluoro-1,4-dihydro-7-(4-methyl)-1-piperazinyl)-4-oxo-3-quinolinecarboxylic acid;
 1-cyclopropyl-6,8-difluoro-1,4-dihydro-7-(4-morpholinyl)-oxo-3-quinolinecarboxylic acid;
 1-cyclopropyl-6,8-difluoro-1,4-dihydro-4-oxo-7-(4-thiomorpholinyl)-3-quinolinecarboxylic acid;
 1-cyclopropyl-6,8-difluoro-1,4-dihydro-4-oxo-7-(1-pyrrolidinyl)-3-quinolinecarboxylic acid;
 1-cyclopropyl-6,8-difluoro-1,4-dihydro-4-oxo-7-(1-piperidinyl)-3-quinolinecarboxylic acid.

EXAMPLE 6

In the same manner as Example 3, the following compounds are prepared from 1-cyclopropyl-6-fluoro-7-chloro-1,4-dihydro-4-oxo-1,8-naphthyridine-3-carboxylic acid (see Example K) and the desired amine or blocked amine:

1-cyclopropyl-1,4-dihydro-6-fluoro-4-oxo-7-(4-thiomorpholinyl)-1,8-naphthyridine-3-carboxylic acid, mp 288°–291° C.
 1-cyclopropyl-1,4-dihydro-6-fluoro-7-(4-morpholinyl)-4-oxo-1,8-naphthyridine-3-carboxylic acid;
 1-cyclopropyl-1,4-dihydro-6-fluoro-4-oxo-7-(1-pyrrolidinyl)-1,8-naphthyridine-3-carboxylic acid;
 1-cyclopropyl-1,4-dihydro-6-fluoro-4-oxo-7-(1-piperidinyl)-1,8-naphthyridine-3-carboxylic acid; and
 1-cyclopropyl-1,4-dihydro-6-fluoro-7-(1-homopiperidinyl)-4-oxo-1,8-naphthyridine-3-carboxylic acid.

PREPARATIVE EXAMPLES FOR INTERMEDIATES

EXAMPLE A

4-[6-(Cyclopropylamino)-3-nitro-2-pyridinyl]-1-piperazinecarboxylic acid, ethyl ester A solution of 126.0 g (0.4 mole) of 4-(6-chloro-3-nitro-3-pyridinyl)-1-piperazinecarboxylic acid, ethyl ester (prepared as described in European Patent Publication No. 9425), 76.1 g (0.5 mole) of 1,8-diazabicyclo[5.4.0]undec7-ene (DBU), 28.6 g (0.5 mole) of cyclopropylamine and 500 ml of absolute ethanol was stirred at room temperature for 48 hours. The solution was then heated at reflux for four hours and concentrated in vacuo. The residue was partitioned between chloroform and water. The chloroform layer was dried over magnesium sulfate and concentrated in vacuo. The residue was triturated with ether to give 64.0 g of the title compound, mp 100°–103° C.

EXAMPLE B

4-[6-(Acetylcyclopropylamino)-3-nitro-2-pyridinyl]-1-piperazinecarboxylic acid, ethyl ester A solution of 64.0 g (0.19 mole) of 4-[6-(cyclopropylamino)-3-nitro-2-pyridinyl]-1-piperazinecarboxylic acid, ethyl ester, 115 ml of acetic anhydride and 115 ml of acetic acid was heated on a steam bath for 36 hours. The solvents were removed in vacuo, the residue was triturated with a mixture of ethanol and toluene which was also evaporated in vacuo to give 68.3 g of the title compound, mp 90°–93° C.

EXAMPLE C

4-[6-(Acetylcyclopropylamino)-3-amino-2-pyridinyl]-1-piperazinecarboxylic acid, ethyl ester A mixture of 17.0 g (45 mmole) of 4-6-(acetylcyclopropylamino)-3-nitro-2-pyridinyl-1-piperazinecarboxylic acid, ethyl ester, 1.5 g of Raney nickel and 180 ml of absolute ethanol was shaken in a atmosphere of hydrogen at about 50 psi and room temperature for approximately 24 hours. The catalyst was removed by filtering through Celite and the solvent removed in vacuo to give 15.2 g of the title compound, mp 149°–150° C.

EXAMPLE D

2-[4-(Ethoxycarbonyl)-1-piperazinyl]-6-(acetylcyclopropylamino)-3-pyridinediazonium tetrafluoroborate A solution of 20.8 g (60 mmole) of 4-[6-(acetylcyclopropylamino)-3-amino-2-pyridinyl]-1-piperazinecarboxylic acid, ethyl ester, 44 ml of ethanol and 27 ml of 48% tetrafluoroboric acid was cooled to 0° C. and treated dropwise with a solution of 4.56 g (66 mmol) of sodium nitrite in 8 ml of water under a nitrogen atmosphere keeping the temperature 0°-5° C. After the addition was complete, the reaction was stirred at 0°-5° C. for one hour and treated with 150 ml of anhydrous ether keeping the temperature below 10° C. The solid was removed by filtration, the precipitate was washed with ethanol/ether (1:1), ether and dried in vacuo to give 24.5 g of the title compound, mp 100°-105° C. (dec.).

EXAMPLE E

4-[6-(Acetylcyclopropylamino)-3-fluoro-2-pyridinyl]-1-piperazinecarboxylic acid, ethyl ester To 800 ml of refluxing toluene was added in portions, as a solid, 46.2 g (0.1 mole) of 2-[4-(ethoxycarbonyl)-1-piperazinyl]-6-(acetylcyclopropylamino)-3-pyridinediazonium tetrafluoroborate. After the addition was complete, the reaction was refluxed for ten minutes and the toluene was decanted from the insoluble precipitate. The toluene was evaporated in vacuo and the residue was partitioned between chloroform and water. The chloroform layer was washed with 5% aqueous sodium bicarbonate, water, dried over magnesium sulfate and evaporated in vacuo to give 13.7 g of the title compound, as a viscous oil. An additional 10.2 g could be obtained by partitioning the original toluene insoluble material in chloroform and water. The organic layer was washed with 5% aqueous sodium bicarbonate, dried over magnesium sulfate, evaporated in vacuo and the residue was chromatographed on silica gel eluting with chloroform/ethyl acetate (6:4). This fraction was also a viscous oil which did not crystallize upon standing. Both fractions were of sufficient purity to be used as is in the ensuing steps.

EXAMPLE F

4-[6-(Cyclopropylamino)-3-fluoro-2-pyridinyl]-1-piperazinecarboxylic acid, ethyl ester A solution of 21.9 g (63 mmole) of 4-[6-(acetylcyclopropylamino)-3-fluoro-2-pyridinyl]-1-piperazinecarboxylic acid, ethyl ester, 170 ml of 15% hydrochloric acid and 235 ml of methanol was refluxed for one hour and allowed to stir at room temperature for 18 hours. The methanol was removed in vacuo and the aqueous acid was made basic with 1.0N sodium hydroxide to pH 10.5. The mixture was extracted with chloroform, the chloroform layer washed with water, dried over magnesium sulfate, and evaporated in vacuo to give 17.6 g of the title compound, mp 68°-70° C.

EXAMPLE G

For Route A

[[Cyclopropyl[6-[4-(ethoxycarbonyl)-1-piperazinyl]-5-fluoro-2-pyridinyl]amino]methylene]propanedioic acid, diethyl ester A solution of 3.8 g (12.3 mmole) of 4-[6-(cyclopropylamino)-3-fluoro-2-pyridinyl]-1-piperazinecarboxylic acid, ethyl ester, 2.7 g (12.3 mmole) of diethyl(ethoxymethylene)malonate and 50 ml of xylene was refluxed for 24 hours. The solvent was removed in vacuo and the residue was chromatographed over silica gel eluting with chloroform/ethyl acetate (80/20) to give 2.3 g of the title compound as a viscous oil which was used without further purification.

EXAMPLE H

For Route A

Ethyl 1-Cyclopropyl-6-fluoro-1,4-dihydro-4-oxo-7-[4-(ethoxycarbonyl)-1-piperazinyl]-1,8-naphthyridine-3-carboxylate A solution of 2.3 g (4.8 mmole) of [[cyclopropyl[6-[4-(ethoxycarbonyl)-1-piperazinyl]-5-fluoro-2-pyridinyl]amino]methylene]propanedioic acid, diethyl ester, in 15 ml of acetic anhydride was treated dropwise with 5 ml of 98% sulfuric acid keeping the temperature 55°-60° C. When the addition was complete, the reaction was stirred for one hour and poured onto 50 g of ice. The aqueous suspension was extracted with chloroform, the chloroform layer washed with water, dried over magnesium sulfate, filtered, and evaporated in vacuo. The residue was triturated with several portions of ethanol/toluene which were also removed in vacuo to give 0.4 g of the title compound, mp 184°-186° C. An additional 0.5 g of product could be obtained by concentrating the original aqueous fraction, mp 184°-186° C.

EXAMPLE I

For Route B

4-[6-[Cyclopropyl(2,2-dimethyl-4,6-dioxo-1,3-dioxan-5-ylidine)amino]-3-fluoro-2-pyridinyl]-1-piperazinecarboxylic acid, ethyl ester A solution of 17.6 g (57 mmole) of 4-[6-(cyclopropylamino)-3-fluoro-2-pyridinyl]-1-piperazinecarboxylic acid, ethyl ester, 11.6 g (63 mmole) of 5-(methoxymethylene)-2,2-dimethyl-1,3-dioxane-4,6-dione and 250 ml of methanol was stirred at room temperature for four hours. The solid was removed by filtration, washed with methanol, ether and dried in vacuo to give 17.6 g of the title compound, mp 177°-178° C.

EXAMPLE J

For Route B

1-Cyclopropyl-6-fluoro-1,4-dihydro-4-oxo-7-[4-(ethoxycarbonyl)-1-piperazinyl]-3-carboxylic acid A solution of 17.0 g (37.0 mmole) of 4-[6-[cyclopropyl(2,2-dimethyl-4,6-dioxo-1,3-dioxan-5-ylidene)amino]-3-fluoro-2-pyridinyl]-1-piperazinecarboxylic acid, ethyl ester in 125 ml of acetic anhydride was treated dropwise with 35 ml of 98% sulfuric acid keeping the temperature 50°-60° C. When the addition was complete, the reaction was stirred for two hours and poured onto 600 g of ice. The mixture was stirred was stirred for one hour and the resulting precipitate was removed by filtration, washed with water and dried in vacuo to give 10.2 g of the title compound, mp 277°-279° C.

EXAMPLE K

1-Cyclopropyl-6-fluoro-1,4-dihydro-7-hydroxy-4-oxo-1,8-naphthyridine-3-carboxylic acid To a solution of 2 ml of 70% nitric acid in 10 ml of 98% sulfuric acid was added in portions 1.0 g (3.0 mmole) of 1-cyclopropyl-6-fluoro-1,4-dihydro-4-oxo-7-(1-piperazinyl)-1,8-naphthyridine-3-carboxylic acid, keeping the temperature between 25°–30° C. The resulting solution was stirred at room temperature for 18 hours and poured onto 40 g of ice. The mixture was stirred at room temperature for 24 hours, concentrated in vacuo, the pH adjusted to 12 with aqueous sodium hydroxide, and filtered through a fiber glass pad. The filtrate was acidified to pH 3.5 with 6.0M hydrochloric acid, the resulting precipitate removed by filtration, washed with water then ether and dried in vacuo to give 0.23 g of the title compound, mp 325°–327° C.

7-Chloro-1-cyclopropyl-6-fluoro-1,4-dihydro-4-oxo-1,8-naphthyridine-3-carboxylic acid A suspension of 0.19 g (0.72 mmole) of 1-cyclopropyl-6-fluoro-1,4-dihydro-7-hydroxy-4-oxo-1,8-naphthyridine-3-carboxylic acid in 2 ml of phosphorus oxychloride was heated at reflux for ½ hour. The resulting solution was cooled to room temperature and the solvent was removed in vacuo. The residue was triturated with ice-water and the resulting solid was removed by filtration, washed with water, then ether and dried in vacuo to give 0.11 g of the title compound, mp 209°–212° C.

EXAMPLE L

1-Cyclopropyl-6,7,8-trifluoro-1,4-dihydro-4-oxo-3-quinolinecarboxylic Acid

2,3,4,5-Tetrafluoro-β-oxo-benzenepropanoic Acid, Ethyl Ester

To 30.0 g (155 mmol) of 2,3,4,5-tetrafluorobenzoic acid in 75 ml of dichloromethane was added 14.8 ml (1.1 equivalents) of oxalyl chloride. The mixture was then treated with three drops of dry N,N-dimethylformamide and the vigorous reaction was stirred at room temperature overnight. The mixture was then concentrated to an oil, taken up in toluene, and reconcentrated to afford 2,3,4,5-tetrafluorobenzoyl chloride which was used in the next step.

To 40.92 g (310 mmol) of malonic acid half ethyl ester in 700 ml of dry tetrahydrofuran at −35° C. was added a stream of n-butyllithium until one equivalent was delivered. The mixture was maintained at −15° to −30° C. during the addition, then warmed to −5° C. treated with 10 mg of bipyridyl. The remainder of the n-butyllithium was added at this temperature until the indicator turned pink. A total of 282 ml of 2.2N n-butyllithium was added. The mixture was recooled to −78° C. and a solution of 2,3,4,5-tetrafluorobenzoyl chloride in 100 ml of dry tetrahydrofuran was added keeping the temperature constant. The reaction mixture was stirred for 45 minutes after the acid chloride addition. It was warmed to −35° C. and poured into 155 ml of 2N hydrochloric acid. To this mixture was added one liter of water and 1.5 liters of dichloromethane. The aqueous phase was separated and extracted with an additional 1.5 liters of dichloromethane. The combined organic phases were washed with 50% saturated sodium bicarbonated and then 1N hydrochloric acid. The dichloromethane was dried (magnesium sulfate) and concentrated to a solid which was triturated with cold pentane to give 37.8 g of 2,3,4,5-tetrafluoro-β-oxo-benzenepropanoic acid, ethyl ester, mp 63°–65° C.

1-Cyclopropyl-6,7,8-trifluoro-1,4-dihydro-4-oxo-3-quinolinecarboxylic Acid

To 17.6 g (66.6 mmol) of the 2,3,4,5-tetrafluoro-β-oxo-benzenepropanoic acid was added 14.6 g (~1.5 equivalents) of triethylorthoformate and 16.19 g (2.38 equivalents) of acetic anhydride. The mixture was refluxed for two hours at 120° (and was then cooled to 80° C. and concentrated in vacuo. The mixture was diluted with t-butanol, cooled to 10° C., and 3.8 g (1.05 equivalents) of cyclopropylamine in 120 ml of t-butanol was added. The mixture was stirred at 20° C. for 30 minutes and then warmed to 50° C. overnight. At this temperature 7.5 g of potassium t-butoxide was added in 50 ml of t-butanol and the mixture was stirred for four hours. It was filtered and the solids dissolved in 250 ml of hot acetic acid and 200 ml of 3N hydrochloric acid was added in portions over four hours at 100° C. The mixture was cooled and the solids collected to give 15.44 g (82%) of the 1-cyclopropyl-6,7,8-trifluoro-1,4-dihydro-4-oxo-3-quinolinecarboxylic acid, mp 226°–228° C.

We claim:

1. A compound of the formula

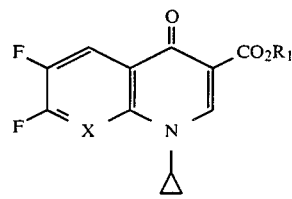

wherein X is N and $R_1$ is hydrogen or lower alkyl, or a pharmaceutically acceptable acid addition or base salt thereof.

2. 1-Cyclopropyl-6-7-difluoro-1,4-dihydro-4-oxo-1,8-naphthyridine-3-carboxylic acid.

3. 1-Cyclopropyl-6-fluoro-7-chloro-1,4-dihydro-4-oxo-1,8-naphthyridine-3-carboxylic acid.

* * * * *